(12) United States Patent
Sagberg

(10) Patent No.: US 10,508,988 B2
(45) Date of Patent: Dec. 17, 2019

(54) METHOD AND SYSTEM FOR GAS DETECTION

(71) Applicant: GasSecure AS, Oslo (NO)

(72) Inventor: Håkon Sagberg, Oslo (NO)

(73) Assignee: GasSecure AS, Oslo (NO)

( * ) Notice: Subject to any disclaimer, the term of this patent is extended or adjusted under 35 U.S.C. 154(b) by 0 days.

(21) Appl. No.: 15/926,574

(22) Filed: Mar. 20, 2018

(65) Prior Publication Data

US 2018/0217055 A1 Aug. 2, 2018

Related U.S. Application Data

(63) Continuation of application No. 14/362,945, filed as application No. PCT/GB2012/053020 on Dec. 5, 2012, now Pat. No. 9,952,143.

(30) Foreign Application Priority Data

Dec. 5, 2011 (GB) .................................. 1120870.9

(51) Int. Cl.
*G01N 21/31* (2006.01)
*G01N 21/3504* (2014.01)
(Continued)

(52) U.S. Cl.
CPC ......... *G01N 21/3504* (2013.01); *G01N 21/59* (2013.01); *G01N 33/0062* (2013.01);
(Continued)

(58) Field of Classification Search
USPC ..................................... 702/24, 50, 181, 188
See application file for complete search history.

(56) References Cited

U.S. PATENT DOCUMENTS

| 4,264,209 A | 4/1981 | Brewster |
| 5,864,293 A | 1/1999 | Lewiner et al. |

(Continued)

FOREIGN PATENT DOCUMENTS

| GB | 2379977 A | 3/2003 |
| WO | 2005003756 A1 | 1/2005 |
| WO | 2009011593 A1 | 1/2009 |

OTHER PUBLICATIONS

International Preliminary Report on Patentability, International Patent Application No. PCT/GB2012/053020, filed on Dec. 5, 2012 (5 pages).

(Continued)

*Primary Examiner* — John E Breene
*Assistant Examiner* — Jeffrey P Aiello
(74) *Attorney, Agent, or Firm* — Haley Guiliano LLP

(57) ABSTRACT

A gas sensor is used for determining a concentration of a predetermined gas in a measurement volume. The gas sensor comprises a light source and a detector arranged to receive light that has passed through the measurement volume. During a first measurement period, the detector is used to make a first measurement of an amount of light received in at least one wavelength band which is absorbed by the gas. The first measurement is compared to a predetermined threshold value. If the threshold is crossed, during a second measurement period the detector is used to make a second measurement of an amount of light received in at least one wavelength band which is absorbed by the gas. The concentration of said gas in said measurement volume is calculated using the first and/or second measurement.

23 Claims, 4 Drawing Sheets

(51) Int. Cl.
*G01N 21/59* (2006.01)
*G01N 33/00* (2006.01)

(52) U.S. Cl.
CPC ............ *G01N 2021/3188* (2013.01); *G01N 2033/0068* (2013.01)

(56) References Cited

U.S. PATENT DOCUMENTS

| | | | |
|---|---|---|---|
| 6,147,351 A | 11/2000 | Huiku | |
| 6,195,581 B1* | 2/2001 | Beerwerth | G01J 5/02 |
| | | | 374/E13.003 |
| 6,348,872 B1 | 2/2002 | Otani et al. | |
| 7,034,943 B1 | 4/2006 | Moeckli et al. | |
| 7,463,420 B2* | 12/2008 | Sagberg | G02B 5/1828 |
| | | | 359/569 |
| 8,948,564 B1* | 2/2015 | Sherman | F21K 9/61 |
| | | | 362/335 |
| 8,953,926 B1* | 2/2015 | Kelly | H05B 33/02 |
| | | | 362/335 |
| 2002/0118116 A1 | 8/2002 | Tice et al. | |
| 2003/0041649 A1* | 3/2003 | George | G01J 3/10 |
| | | | 73/24.02 |
| 2005/0062972 A1 | 3/2005 | Krusen | |
| 2005/0068612 A1* | 3/2005 | Wilson | H01S 3/1301 |
| | | | 359/337 |
| 2005/0225840 A1 | 10/2005 | Drasek et al. | |
| 2006/0173637 A1* | 8/2006 | Martin | G01D 3/036 |
| | | | 702/24 |
| 2006/0254911 A1* | 11/2006 | Lindmueller | G01N 33/0062 |
| | | | 204/424 |
| 2007/0017458 A1 | 1/2007 | Frodl et al. | |
| 2007/0097349 A1* | 5/2007 | Wada | G01S 7/493 |
| | | | 356/4.06 |
| 2007/0258083 A1* | 11/2007 | Heppell | A61B 5/14532 |
| | | | 356/39 |
| 2008/0049231 A1* | 2/2008 | Bachalo | G01N 15/1459 |
| | | | 356/484 |
| 2010/0007890 A1* | 1/2010 | Graf | G01N 21/3504 |
| | | | 356/437 |
| 2010/0063748 A1* | 3/2010 | Mottier | G01N 21/3504 |
| | | | 702/24 |
| 2011/0077459 A1* | 3/2011 | Rofougaran | G06F 19/3418 |
| | | | 600/103 |
| 2011/0184624 A1 | 7/2011 | Han et al. | |
| 2012/0287418 A1* | 11/2012 | Scherer | G01N 21/61 |
| | | | 356/51 |

OTHER PUBLICATIONS

International Search Report on Patentability, International Patent Application No. PCT/GB2012/053020, filed on Dec. 5, 2012 (10 pages).

UK Search Report, GB Application No. GB1120870.9, dated Mar. 30, 2012 (4 pages).

* cited by examiner

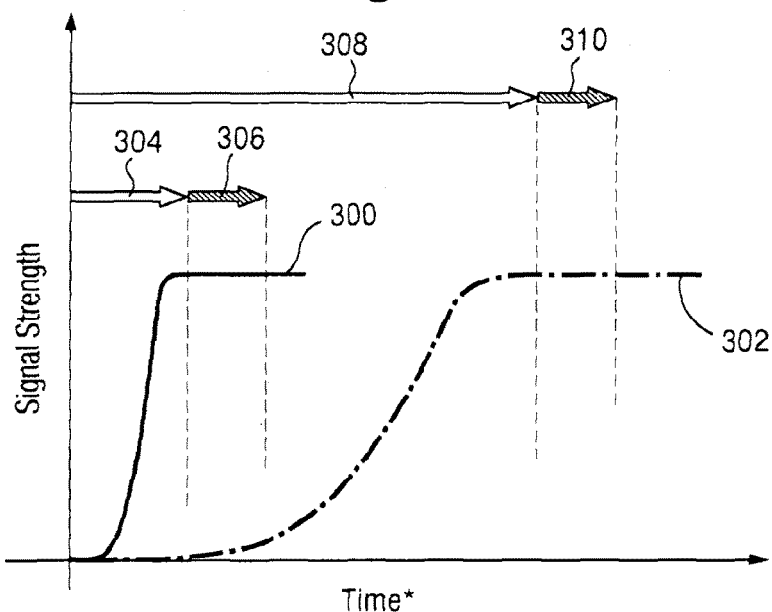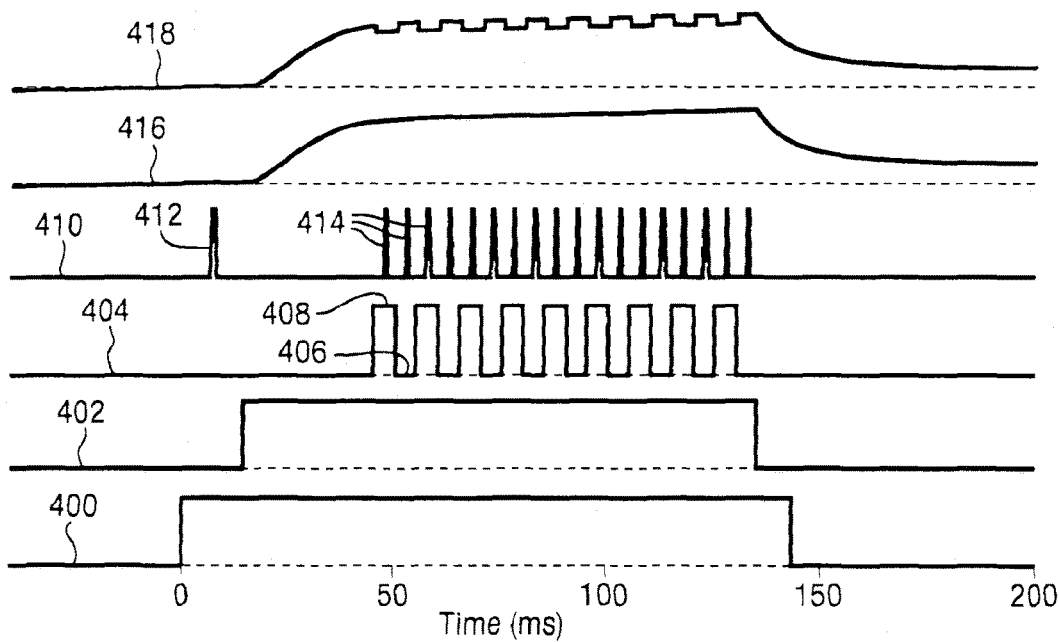

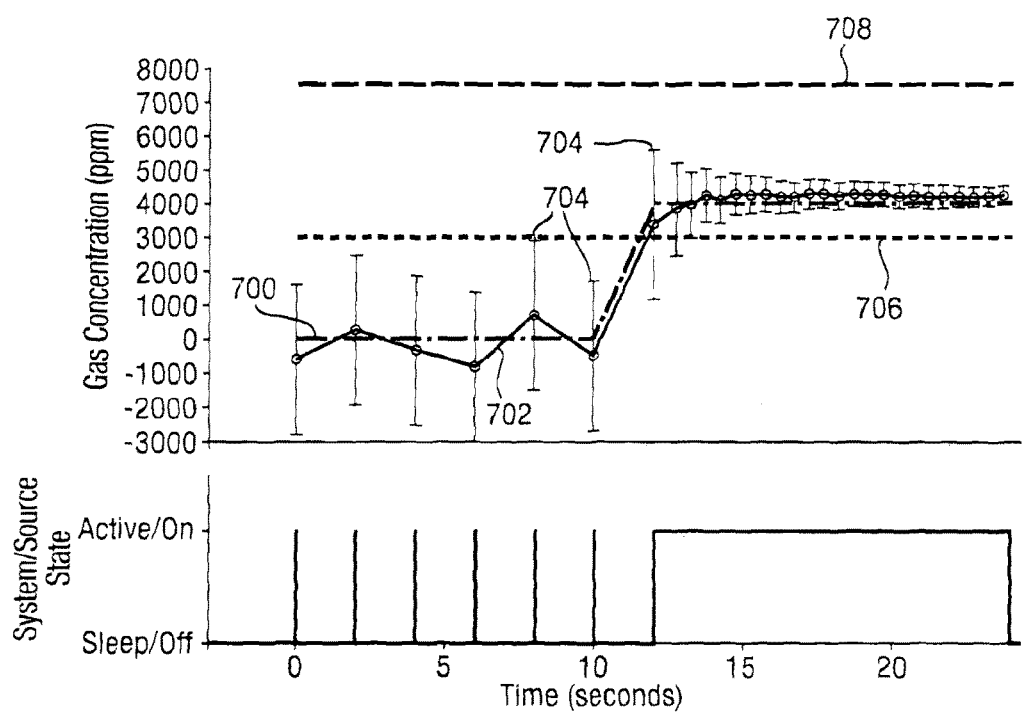

METHOD AND SYSTEM FOR GAS DETECTION

CROSS-REFERENCE TO RELATED APPLICATIONS

This application is a continuation of U.S. patent application Ser. No. 14/362,945, filed on Jun. 5, 2014, which is a U.S. National Stage entry under 35 U.S.C. § 371 based on International Application No. PCT/GB2012/053020, filed on Dec. 5, 2012, which has published under PCT Article 21(2) and which claims priority to British Patent Application No. 1120870.9 filed on Dec. 5, 2011.

FIELD OF THE INVENTION

This invention relates to a method and system for gas detection, more specifically for reduction of the energy consumption of a gas sensor.

BACKGROUND OF THE INVENTION

In order to monitor the gas composition in a gas mixture such as the amount of hydrocarbons in air in a production facility or the gas composition in reactor systems gas sensors are utilized being positioned in chosen locations to monitor the gas composition and/or detect chosen gases. Traditionally these sensors have been limited by the fact that they require power and communication connections, which make installation expensive, make it difficult to move or add sensors and limits the possible locations of the sensors.

Thus there is a need for a gas sensor which can be operated without power supply and communication lines. Long maintenance intervals for fixed gas detectors require long battery lifetime. Reliability of gas sensors requires short response time and thus frequent or continuous measurement. Earlier technology for reliable gas sensors was not capable of providing wireless monitoring with long battery lifetime and short response time because of the high energy consumption it required.

A gas sensor with lower energy consumption will also be an advantage in portable gas detectors, enabling smaller battery pack and/or longer battery life.

One proposed solution is described in Norwegian patent 327678 (see also WO 2009/011593) where two sensors are used. The first sensor is a non-specific sensor with low energy consumption which detects changes in the concentration of one or more gasses in the environment. The second sensor is specific but has higher energy consumption. When the first sensor detects a change in the gas concentration it activates the second sensor so as to detect whether there is an increase in the concentration of one specific gas. This solution results in an energy consumption being significantly less than would be the case if the second sensor was active continuously.

A related solution is described in US2010/0089122 where a gas sensor monitors a gas in a mixture and where the detection of the gas starts by pulsing a heat source in order to increase the accuracy of a quantitative measurement of the gas. The heating is in this case for avoiding saturation problems in the sensor cell but a hibernation method is used for saving energy. However, the energy consumption is still too high to be used in a solitary sensor.

SUMMARY OF THE INVENTION

When viewed from a first aspect the invention provides a method of operating a gas sensor for determining a concentration of a predetermined gas in a measurement volume, the gas sensor comprising a light source and a detector arranged to receive light that has passed through the measurement volume, the method comprising the steps of:
  during a first measurement period, using the detector to make a first measurement of an amount of light received in at least one wavelength band which is absorbed by the gas;
  comparing said first measurement to a predetermined threshold value;
  if said threshold is crossed, during a second measurement period using the detector to make a second measurement of an amount of light received in at least one wavelength band which is absorbed by the gas; and
  calculating the concentration of said gas in said measurement volume using the first and/or second measurement.

When viewed from a second aspect the invention provides a gas sensing system including a gas sensor comprising a light source, a measurement volume and a detector arranged to receive light that has passed through the measurement volume, the system being arranged to:
  during a first measurement period, use the detector to make a first measurement of an amount of light received in at least one wavelength band which is absorbed by the gas;
  compare said first measurement to a predetermined threshold value;
  if said threshold is crossed, during a second measurement period using the detector to make a second measurement of an amount of light received in at least one wavelength band which is absorbed by the gas; and
  calculate the concentration of said gas in said measurement volume using the first and/or second measurement.

When viewed from a third aspect the invention provides a wireless gas sensor comprising a light source, a measurement volume and a detector arranged to receive light that has passed through the measurement volume, the sensor being operable in a first mode in which it measures an amount of light received by the detector in at least one wavelength band which is absorbed by the gas based on a first amount of light sampled; and in a second mode in which it measures an amount of light received by the detector in at least one wavelength band which is absorbed by the gas based on a second amount of light sampled; wherein said second amount of light is greater than the first amount of light.

At least some embodiments of the invention provide a gas measuring method and system which can be positioned independently of any external power supply and communication line, and which also can provide measurements within a certain level of accuracy and with a short response time.

In optical gas detection the usual method is to emit light from a known source having a known spectrum and seeing how the light is changed by interacting with the gas molecules at different wavelengths. How accurately this change is measured depends on a number of factors, such as the intensity and wavelength of the source spectrum, the propagation length of the light through the gas, type of detector element, how long the detector is exposed to the light etc. Often the light source will be the component having the highest energy consumption during the measurements. Time and intensity control of the source will therefore be important parameters for making a high efficiency sensor system.

The important point is to control the detector system signal to noise ratio (SNR) and thus the accuracy, so that deviating conditions in the gas mixture may be detected within a predetermined reliability margin. Simplified one may say that the SNR is proportional to the power of the light source multiplied with the square root of the measuring period.

To take one non-limiting example, for a sensor to be used for detection of hydrocarbon leakages in safety systems there is a need for fast response, typically less than 5 seconds. More generally the required rate and/or accuracy of the measurements will depend of the gas to be detected and the danger involved if the concentration exceeds a chosen limit, and may increase with higher concentrations.

It will be seen by those skilled in the art that in accordance with the present invention the gas sensor can be used in two different measurement modes but based on the same detector arrangement. Thus a relatively cruder/less accurate, but more energy efficient measurement can be taken most of the time, but if this indicates a potentially dangerous concentration of gas, a second measurement period is used which will consume more energy but will give a more accurate estimate of the gas concentration.

The first measurement mode has a low energy consumption and can thus be used for high frequency or essentially continuous monitoring of the gas mixture, called the ground state and then, if necessary the second mode can be activated which can be seen as a 'quantification state' adapted to provide more accurate measurements of the concentration of the specified gas if a certain threshold is crossed based on the first measurement.

The invention may be used to monitor for dangerously high levels of a gas (e.g. hydrocarbon) or dangerously low levels of a gas (e.g. oxygen) and thus the threshold to trigger the second measurement period may be a maximum or minimum threshold.

The second measurement could be completely independent of the first measurement or might be an extension of it. Thus in one set of embodiments the second measurement period is simply used to gather more samples in the same way as for the first measurement period. This has an advantage in that system stability is improved and systematic errors are also reduced.

The gas concentration calculated could be based only on the second measurement, but in a set of preferred embodiments it is based on the first and second measurements. This allows use to be made of the first measurement whilst improving its accuracy using the second measurement. For example the first measurement could comprise a certain number of samples and the second measurement would give additional samples with the gas concentration being calculated as an average of all of the samples.

As mentioned above the second measurement period may simply comprise measuring the amount of light in the wavelength band absorbed by the predetermined gas in the same way as for the first measurement period for a longer period. Alternatively however the second measurement period mode may involve an increased light intensity during the second measurement and/or an increased sampling rate. Thus one set of embodiments comprises carrying out the first measurement at a first sampling rate and carrying out the second measurement at a second sampling rate which is higher than the first sampling rate.

Another set of embodiments comprises carrying out said first measurement with the light source at a first intensity and carrying out said second measurement with the light source at a second intensity which is higher than the first intensity.

The source intensity may in some embodiments be controlled by changing the applied voltage, but this will change the source temperature and thus the shape of the emitted spectrum, which in turn will reduce the accuracy of the result of the measurements. According to a preferred set of embodiments the light source comprises a variable light emitting area so that the emitting surface area of the light source can be increased between the first and second measurement periods.

In a preferred set of embodiments the light source comprises at least two areas able to emit light within the same range of wavelengths. The emitting surface area of the light source can thus be increased by increasing the number of areas which are active, i.e. emitting light.

A preferred example of such a light source is a micro-electro-mechanical system (MEMS) or a micro-fabricated device, as will be discussed below. These light sources would typically require that the sensor is arranged so as to project the complete active area of the source onto the detector. A MEMS based infra-red source has additional advantages in that it has a lower heat capacity and a shorter response time than alternative light sources. It will be more energy efficient than an ordinary light bulb/filament source.

In a preferred set of embodiments the system comprises an adaptable filter disposed between the light source and the detector and having a measurement state in which it passes at least one wavelength band which is absorbed by the gas and a reference state in which said wavelength band is attenuated relative to the measurement state.

This is advantageous as it allows a single source and single detector to be used whilst allowing for full compensation since the 'active; and 'reference' measurements are taken using exactly the same optical path. This enables its power consumption to be low and facilitates a remote, battery-powered wireless sensor unit with long battery life.

Preferably the light source is arranged to emit pulses of light and the adaptable filter is arranged to change between one of said measurement state and said reference state to the other at least once during each pulse. This allows a fully compensated measurement to be taken in a single pulse of light thus making the measurement highly energy efficient.

In accordance with the embodiments of the invention described above the adaptable filter directs the light from the source onto the detector. By changing its state, the wavelength spectrum of light it passes is changed. Preferably it comprises a micro-electromechanical system (MEMS). These can be fabricated so as to be able to change the wavelength spectrum of light passed. The spectrum change can be performed on a timescale less than one millisecond which means that a short pulse of light can be used whilst still giving both a measurement and reference period, thereby limiting the power consumption associated with the measurement. The MEMS could comprise a diffractive optical element having a plurality of grating bands arranged to be moved by an electrostatic potential.

The MEMS solution is particularly convenient for 'cold starting' the sensor system and performing a complete measurement using a single pulse of light. This can be done because the spectrum modulation can be so fast that drift or low-frequency noise can be filtered, and because the 'active' and 'reference' wavelengths are measured using exactly the same light path. Drift, non-uniformity, and other error sources will affect the two measurements equally.

As used herein the term 'pulse' as applied to light is intended to mean a temporary emission or increase in light output. No particular pulse shape is to be inferred and it is not necessarily the case that outside of pulses there is no light emission. The length of a pulse may be defined as the length of time for which the light is above a predetermined threshold. The pulse width may be varied in accordance with the invention as set out herein.

Where the calculated gas concentration is based on the first and second measurements, and/or increased light intensity and/or increased sampling rate the second measurement period may be able to be shorter than the first measurement period and still be more accurate. Typically however the second measurement period is the same length as, or longer than, the first measurement period.

Whether it is through a longer measurement period, more intense light, more frequent samples, or any combination of these, use of the second measurement period in accordance with the invention increases the amount of light on which the calculation of gas concentration is based and so therefore improves the SNR which in turns enhances the accuracy of the estimate of concentration.

In preferred embodiments the system will be tolerant to both random and systematic errors in the first mode, as well as signal drift, since measurement errors will almost certainly cause the system to switch to the second mode. In addition to increasing the amount of light detected, the second mode may also use different methods for compensation or calibration than the first mode.

The appropriate increase in emitted power, sampling rate or measuring time may be found empirically or based on a theoretical model. Thus the light emission or measuring time may either be pre-calculated or calculated on the fly by analyzing the SNR of the measured signal within the measuring time window.

The SNR of the detector signal may be measured as the mean value of the signal energy divided by the variance over a measuring interval where the incoming signal is expected to be constant. For a sensor according to preferred embodiments of the invention the signal may be a high frequency AC signal (e.g. 1 kHz) overlaid on a low frequency base signal. The high frequency signal is caused by a wavelength filter modulation and is related to the strength of the gas absorption, while the low frequency base signal comes from the light source modulation and is related to light intensity. Alternatively the modulation may be provided by use of two light sources and/or detectors where the light sources are modulated, not the filter. An increase in the length of the measuring window (but using the second measurement period) will reduce the standard deviation and thus increase the SNR of the modulation signal.

If the SNR is underestimated because of rapid changes in gas concentration, the system will switch to the second mode in which the second measurement period is used, This is a desired property of the system because in this case accurate concentration measurements are needed continuously.

The detector signal SNR, accuracy, error sources etc may also be estimated from a table of values. The table for SNR may then be specified from the length of the measuring window (e.g. the length of the first and second measurement periods assuming that both the first and second measurements are used), the voltage applied to the light source, the number of source elements in use, for how long the source has been on or other parameters affecting the source and detector with related electronics. The table may be made from calibrated measurements of SNR under controlled conditions as part of the source production and parameter settings, or may be made from data simulations.

A first calculation example shows the parameters that may affect the SNR:

For infrared gas concentration measurements, we may define a signal x that represents the reduction of light intensity caused by the gas in the measurement volume. The Signal-to-Noise Ratio (SNR) of the signal x can then be defined as $$SNR = \frac{\mu}{\sigma}$$

where the expected value $\mu$ can be estimated as the mean value x over n measured values $x_i$:

$$\bar{x} = \frac{1}{n}\sum_{i=1}^{n} x_i$$

and $\sigma$ is an estimate of the standard deviation of the noise $$\sigma = \sqrt{\frac{1}{n-1}\sum_{i=1}^{n}(x_i - \bar{x})^2}.$$

For normally distributed and statistically independent measuring values, the standard deviation of the mean value averaged over n measured values can be estimated as $$\hat{\sigma}_{\bar{x},n} = \frac{\sigma}{\sqrt{n}}$$

When averaging n measurements, it is reasonable to assume with 99.9% certainty that $\mu$ (the expected value of x) is lower than the mean of the measurements plus three standard deviations:

$$\mu < \bar{x} + 3\hat{\sigma}_{\bar{x},n}.$$

In order to check if the true value of x is below a threshold value $x_T$, so that system may go back to its energy efficient mode of operation, the measurements should be continued until:

$$\bar{x} < x_T - 3\hat{\sigma}_{\bar{x},n} = x_T - \frac{3\sigma}{\sqrt{n}}$$

A similar discussion may be done based on a continuous measurement in an increased time window.

One set of embodiments comprises determining one or more of the length of the second measurement period, the second sampling rate or the second intensity using a temperature of the gas sensor.

One set of embodiments comprises determining one or more of the length of the second measurement period, the second sampling rate or the second intensity using the first measurement.

A set of embodiments comprises estimating a value of an uncertainty parameter indicative of the level of uncertainty of the first measurement and determining one or more of the length of the second measurement period, the second sampling rate or the second intensity using the value of the uncertainty parameter.

A set of embodiments comprises estimating a value of an uncertainty parameter indicative of the level of uncertainty of the calculated concentration of gas and ending said second measurement period if said value is below a predetermined minimum.

A set of embodiments comprises ending said second measurement period if the calculated concentration of gas crosses a predetermined threshold.

The first measurement is preferably carried out continually at a rate chosen so that the concentration of the gas is not expected to change significantly between two measurements.

However in accordance with some embodiments set out above, the system effectively continuously monitors the measurements and adaptively switches the sensor between the two measurement modes by switching the second measurement period on when measurements during the first measurement period indicate a gas concentration crossing a certain threshold and switching the second measurement period off when the measurements made using the second measurement period confirm that the gas concentration no longer crosses a threshold.

BRIEF DESCRIPTION

Certain embodiments of the invention will be described, by way of example only, with reference to the accompanying drawings in which:

FIG. 3 illustrates the energy consumption advantages related to a MEMS source compared to a light bulb/filament source related to energy consumption;

FIG. 4 illustrates the measuring sequence including modulation of the filter according to a preferred embodiment of the invention;

FIG. 7 shows a plot illustrating the measurements and uncertainty when gas concentration is increased to a above the critical level.

DETAILED DESCRIPTION

Figure 1:
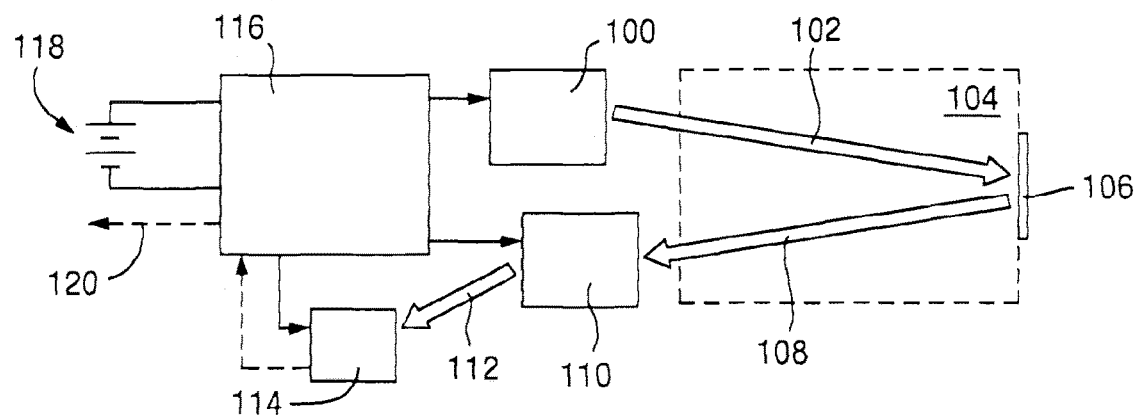
FIG. 1 is a block diagram illustrating the sensor system according to a preferred embodiment of the invention, with signal paths for light, sensor signal and control signals.

Referring to FIG. 1 a system according to a preferred embodiment of the invention will be described. The system comprises an infrared (IR) source 100 emitting light 102 through a measuring cell/measuring path 104 where, if the target gas is present, light will be absorbed at specific wavelengths being characteristic for the target gas. In FIG. 1 the light 102 propagates across the measuring cell 104 to a mirror 106 and is reflected back. The reflected light 108 propagates toward a controllable filter 110 filtering light 112 to one or more of said characteristic wavelengths in a manner alternating with light at one or more reference wavelengths which are detected at a detector 114. The control unit 116 controls both the light source 100, the filter 110 and the detector 114 and is powered by a battery 118.

In order to measure the gas concentration in short time windows the light source 100 is preferably a MEMS source having a short rise time providing an adjustable pulse length in the range of 1-1000 ms as will be discussed in relation to FIG. 3.

The controllable filter is capable of shifting between a reference wavelength outside the gas absorption spectrum and a measuring wavelength within the absorption spectrum, during said time window so as to provide both a reference signal and a measuring signal, as will be discussed in relation to FIG. 4. This shifting may be performed using a filter made from a diffractive element as described in U.S. Pat. No. 7,463,420, WO2011/018521 or paper by Sagberg et al: "Two-state Optical Filter Based on Micromechanical Diffractive Elements" published in International Conference on Optical MEMS and Nanophotonics, 2007 IEEE/LEOS, Issue Date: Jul. 16-Aug. 12, 2007. This filter may for example be configured to alternate between reflecting light at two different wavelength ranges toward the detector. Knowing the timing of the filters the control unit may distinguish between the gas and reference measurements.

The ratio between the intensity at the gas wavelengths and the intensity at the reference wavelengths provides a measurement of the concentration of the target gas in the cell 104 or measuring path 102, 108. Light having the selected wavelength spectrum is transmitted from the controllable filter 110 to a photo detector 114 which measures the light intensity. The measuring voltage provided from the photo detector 114 is converted into a digital signal 120 in the micro controller 116 which also controls the clock determining the length of the time windows and the interval between them, and/or the state and area of the source 100 and the controllable filter 110. The micro controller 116 may also control the voltage from the power supply applied on the source 100 and the filter 110.

It is an object of at least preferred embodiments to obtain measurements with known and controlled accuracy and with low energy consumption. In order to obtain this the sensor is adapted to shift between a ground state and measuring state, or be controlled continuously from a rest state to a measuring state having a specified reliability. As a measure of the reliability, an estimate of the uncertainty of each measuring sequence may be provided based on the SNR in each sequence. A measuring sequence may comprise a number of single measurements of the sensor voltage on the photo detector with alternating light from the reference wavelength and gas wavelength using a controllable filter as described above. The SNR may be increased by increasing the intensity of the light source, i.e. increasing the amount of light going through the measuring cell or path, by increasing the time window used for measurement or by increasing the sampling rate, i.e. the number of measurements in each sequence, or any combination of these.

Figure 2:
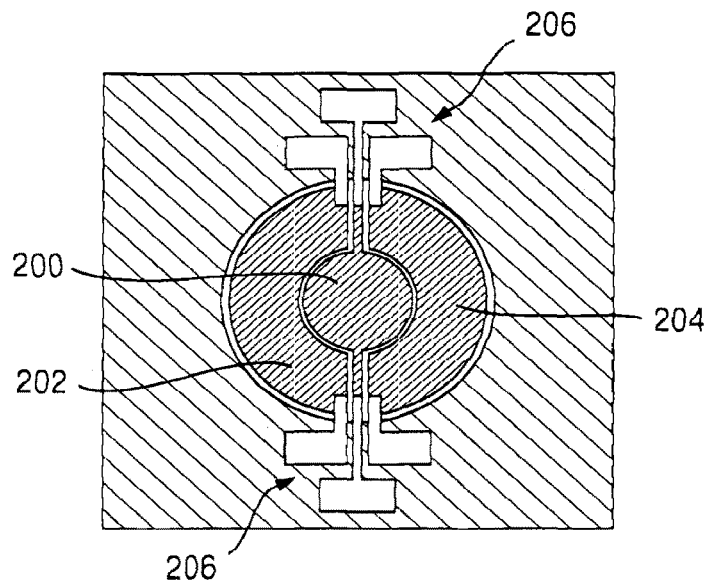
FIG. 2 illustrates a two-step source having two controlled emission areas so as to provide two different source sizes.

The amount of light into the measuring cell may be controlled by having a source with an emitting area that may be changed, as illustrated in FIG. 2. This will be advantageous over an increase in the voltage and thus the temperature of the source as this will change the emitted spectrum of the source. The preferred embodiment will be a MEMS source 100 having an emission area that can be changed. FIG. 2 illustrates an example of such a configuration being constituted by three segments: one central disc 200, and two concentric ring segments 202, 204. The three areas 200, 202, 204 have respective individually addressable current supplies through contacts 206. The three areas are controlled so as to obtain the same working temperature and thus spectrum. As an alternative it is also possible to use a light source having a variable working temperature in combination with compensation through calibration, or with an adaptive filter providing light at comparable spectra with different intensity even when the light source has different temperatures.

A MEMS source will have an emission area with very low thermal mass, which reduces the amount of energy transferred, and enables it to attain the correct emission temperature fast. This way the source may be pulsed with short pulse lengths (low energy per pulse) and a high pulse rate (giving flexible modulation rate), which may be used on the detector part with heterodyne detection whereby the detector is controlled in sync with the source so that unwanted contributions are evened out.

A MEMS source is not essential however, customized light bulbs or other filament sources with one or more separately addressable filaments may be used, but at the cost of reducing the possibility for short pulses and high pulse rate. The emission areas of filaments may have different shapes as long as they are made to obtain the same spectrum, i.e. usually the same temperature. Temperature control means or coatings for controlling the emission of each filament may also be contemplated.

FIG. 3 illustrates the relationship between the signal on the detector, the time lapsed during a pulse and the energy consumption when turning on a MEMS and an incandescent/filament source respectively. A signal 300 is produced on the detector by a MEMS source in accordance with the preferred embodiment of the invention and a corresponding signal 302 is produced for a filament source. The MEMS source has a warm-up phase 304 followed by a measurement phase 306, and the filament source has a warm-up phase 308 followed by a measurement phase 310. As can be seen, the incandescent lamp has a higher heat capacity and thus obtains a maximum intensity at a later stage than the MEMS source. For the MEMS source the duration of the warm-up phase 304 is comparable to the duration of the measurement phase 306 but for the incandescent source the duration of the warm-up phase 308 is much longer than the duration of the measurement phase 310 (which is the same as the duration of the measurement phase 308) This in turn results in a higher energy consumption and lower pulse rate than can be achieved with the MEMS source.

FIG. 4 illustrates the use of the adaptable filter according to a preferred embodiment of the invention as mentioned above. The lowermost line 400 illustrates the state of the microcontroller when it is in the active, measurement mode, and line 402 illustrates the lamp power being turned on at a predetermined time.

Line 404 indicates infrared filter control, and illustrates the switching of the filter between two states 406, 408 in which it passes different sets of wavelengths: one is a reference set of wavelengths and the other is the measurement set that includes the characteristic wavelengths of the gas to be detected. This is performed in a sequence during a predetermined time within the active part of the cycle.

Line 410 indicates signal sampling, and illustrates the sampling sequence of the detector, including a first background sampling 412 before the activation of the lamp, and then a sampling 414 in each state of the filter sequence, i.e. each time the filter switches wavelength range, the intensity is sampled for that wavelength range.

The two uppermost lines 416, 418 in FIG. 4 indicate the detector signals and illustrate the difference between the measurements with a gas present (top line 418) and without a gas present (second line down 416). As can be seen, the detector will not see any difference in received intensity if no gas is present, but if a gas is present an increase amount of light is absorbed in the gas and there will be a difference in the detected intensity inside or outside the specific wavelength associated with the gas to be detected. Thus the difference between the sampled intensities in the two states can be used to give a measurement of the concentration of the specified gas, and the variation between the samples in the sequence may indicate the uncertainty in the measurement, which then may be reduced by increasing the intensity of emitted light and/or the sampling period, and/or the sampling rate.

Figure 5:
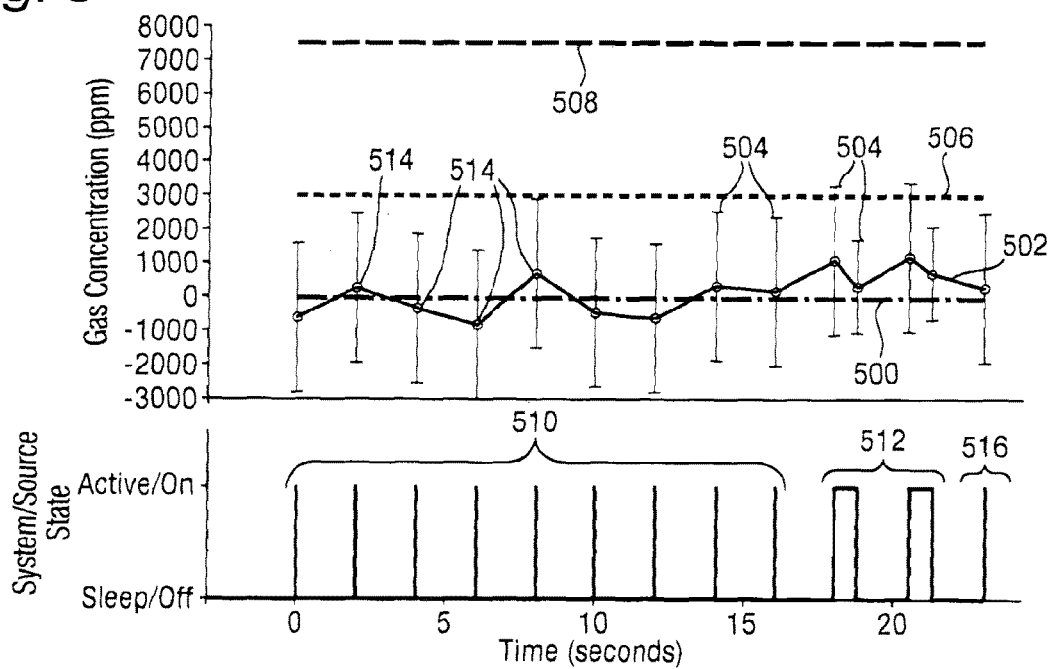
FIG. 5 shows a plot illustrating the measurements and uncertainty when gas concentration is at a low level.
Figure 6:
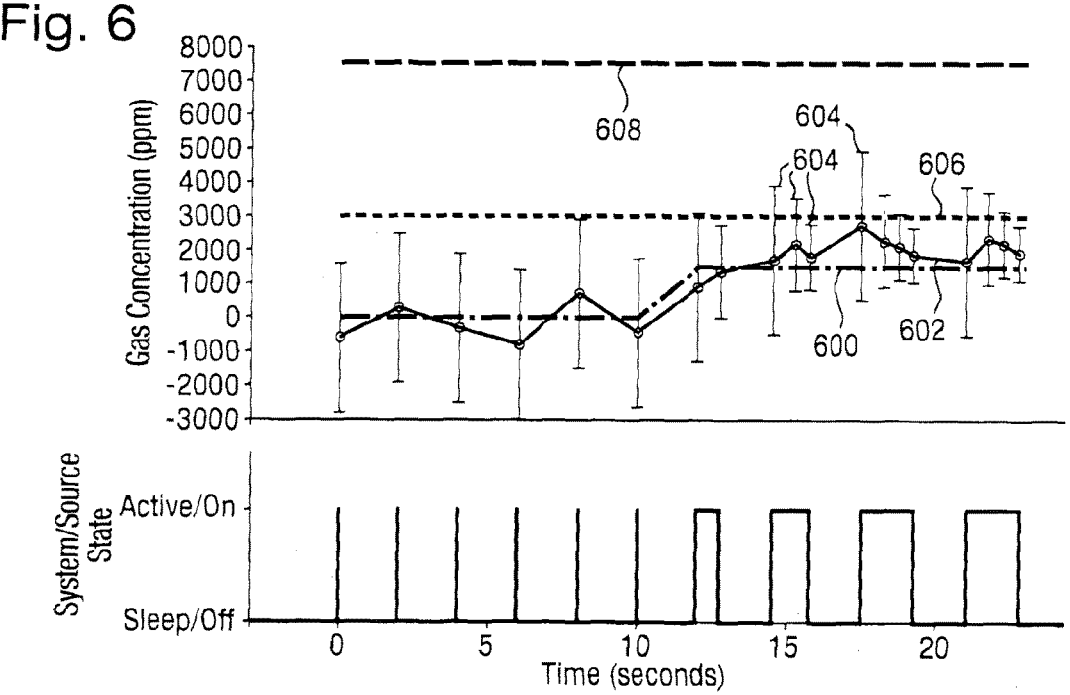
FIG. 6 shows a plot illustrating the measurements and uncertainty when gas concentration is increased to a sub critical level.

How the SNR is controlled during the measuring sequences is illustrated in FIGS. 5-7. In normal operation the sensor is set to monitor the situation with little or no gas present. In such normal operation it makes a continual series of first measurements which are configured to be energy efficient. However the sensor is also set to provide accurate measurements of the concentration when the first measurement corresponds to a concentration above a chosen threshold level by increasing the length of time for which samples are taken in each cycle. At the same time a notice may be provided to an operator. In order to reduce energy consumption the system is arranged to be in a state of hibernation between the measuring sequences.

FIG. 5 illustrate how the sensor system is in the base condition, where the measurements are performed at sufficiently short intervals relative to the required response time as not to allow the gas concentration to change significantly within the interval. FIG. 5 shows the true concentration 500 of the gas, the measured concentration 502 of the gas with a confidence interval 504 of each measurement, a trigger threshold 506 and a lower alarm level 508. In the initial state the sensor is clocked so as to activate the controller to perform a short measuring sequence after which the sensor is returned to hibernation before a new clock pulse initiates the controller. There are several ways of performing the short cyclic base or first mode 510 (Mode 1) measurements and the longer second mode 512 (Mode 2) measurements respectively. One preferred method is to use the sequence shown in FIG. 4 where the difference between Mode 1 and Mode 2 is the length of the sequence (number of samples/filter switching cycles).

In FIGS. 5-7 the initial measurements 514 are performed at two second intervals. In FIG. 5 this is maintained until fluctuations make the confidence interval 504—that is the measured value plus the estimate of uncertainty in the measured value—rise above a threshold trigger level 506 after 18 seconds. This causes the sensor to switch into a second mode 512 where a second measurement period is undertaken, having the effect of increasing the length of the time window of that measuring sequence. The second measurement period continues until it can be ascertained that the aforementioned confidence interval 504 has been reduced below and remains below the threshold level 506. The same is repeated in the next sample window. After this the sensor returns to hibernation level in the first mode 516 until the next measuring interval begins and the same sequence is repeated until it again returns to hibernation mode.

FIG. 6 shows a true concentration 600 of a gas, a measured concentration 602 of the gas with a confidence interval 604 of each measurement, a trigger threshold 606 and a lower alarm level 608. FIG. 6 illustrates how the gas concentration 600 is increased from zero to a value below the critical concentration 606, which is below the alarm level 608. In the same way as for FIG. 4, the controller initiates a second measurement period which increases the length of the measuring sequence when the uncertainty 604 is above the threshold or trigger level 606, but in this embodiment the second measurement period is extended in steps of two and three until the confidence interval 604 is below the trigger level 606.

FIG. 7 shows a true concentration 700 of a gas, a measured concentration 702 of the gas with a confidence interval 704 of each measurement, a trigger threshold 706 and a lower alarm level 708. FIG. 7 illustrates the situation in respect of another embodiment when the gas concentration 700 increases until it is above the trigger level 706. In this embodiment the sensor will then switch to continuous measurement with maximum accuracy and provide the measured concentration 702 as an output signal. If a higher, alarm level 708 is exceeded, an alarm message may be sent.

In addition to or as an alternative to increasing the length of the time window at the detection of a confidence interval rising above the trigger level, the interval between equal time windows may be reduced, i.e. the sampling rate is increased. The measurements in these adjacent time windows are used for calculating the accuracy of the measurements and determining whether the concentration has increased above the critical value.

In accordance with the described embodiments, the threshold will provide a trigger level indicating a need for a further investigation of the gas concentration to be performed automatically and possibly also generating a warning signal or alarm. The threshold may be a chosen limit comparable to the measurements and may also take into account the measured or calculated uncertainty of the signal measured in the first step. The warning or alarm signal may only be given if a second alarm level is detected, e.g. indicating a dangerous gas concentration.

The increase in sampled amount of light may be performed by increasing the length of time in which the light is sampled within the range in which the source is emitting or by adjusting the source emission time. During the time window the uncertainty may be analyzed through the variations in the sampled signal or according to a predefined or calculated table of uncertainty vs sampling time. The time window length may then be increased until the analysis or table indicate an uncertainty being less than a predetermined value.

Another way to increase the amount of light sampled is to increase the sampling rate, or number of sequential samples. The increase may be by a fixed amount or progressively until the analysis of the variation in the sampled data has an uncertainty which allows certainty that the measurement is within the chosen threshold or alarm level.

Another way of increasing the amount of light sampled is to increase the intensity of said light source within said characteristic wavelength range. This may be performed using a light source comprising at least two areas or filaments emitting light within the same range of wavelengths, the increase in said intensity being achieved by increasing the number of emitting areas. Alternatively the source temperature may be increased and the emitted light filtered so that the spectrum received at the detector is comparable, or the detector is calibrated differently for the two different temperatures. In any case the temperature of the sources should be controlled.

What is claimed is:

1. A method of operating a gas sensor for determining a concentration of a gas in a measurement volume, the gas sensor comprising a light source and a detector arranged to receive light that has passed through the measurement volume, the method comprising the steps of:
   during a lower energy consumption measurement period, using the detector to make a lower energy consumption measurement of an amount of light received in at least one wavelength band which is absorbed by the gas;
   comparing said lower energy consumption measurement to a threshold value;
   if said threshold value is crossed, during a higher energy consumption measurement period using the detector to make a higher energy consumption measurement of an amount of light received in at least one wavelength band which is absorbed by the gas; and
   calculating the concentration of said gas in said measurement volume using the lower energy consumption and/or the higher energy consumption measurement;
   wherein the gas sensor comprises a temperature sensor, the method further comprising using a temperature of the gas sensor to configure one or more of a length of the higher energy consumption measurement period, a sampling rate at which the higher energy consumption measurement is carried out or an intensity of the light source during the higher energy consumption measurement period.

2. The method as claimed in claim 1, further comprising carrying out said lower energy consumption measurement at a first sampling rate and carrying out said higher energy consumption measurement at a second sampling rate which is higher than the first sampling rate.

3. The method as claimed in claim 1, further comprising carrying out said lower energy consumption measurement with the light source at a first intensity and carrying out said higher energy consumption measurement with the light source at a second intensity which is higher than the first intensity.

4. The method as claimed in claim 3, further comprising increasing an emitting surface area of the light source between said lower energy consumption measurement period and said higher energy consumption measurement period.

5. The method as claimed in claim 4, wherein the light source comprises at least two areas able to emit light within the same range of wavelengths, and the step of increasing the emitting surface area of the light source comprises increasing the number of said areas which are emitting light.

6. The method as claimed in claim 1 comprising determining one or more of a length of the higher energy consumption measurement period, the sampling rate at which the higher energy consumption measurement is carried out or the intensity of the light source during the higher energy consumption measurement period using the lower energy consumption measurement.

7. The method as claimed in claim 1, further comprising estimating a value of an uncertainty parameter indicative of a level of uncertainty of said lower energy consumption measurement and determining one or more of the length of the higher energy consumption measurement period, the sampling rate at which the higher energy consumption measurement is carried out or the intensity of the light source during the higher energy consumption measurement period using the value of said uncertainty parameter.

8. The method as claimed in claim 1, further comprising ending said higher energy consumption measurement period if the calculated concentration of gas crosses a threshold.

9. The method as claimed in claim 1, wherein an adaptable filter is disposed between the light source and the detector, said adaptable filter having a measurement state in which it passes said wavelength band which is absorbed by the gas and a reference state in which said wavelength band is attenuated relative to the measurement state.

10. The method as claimed in claim 9, further comprising the light source emitting pulses of light and the adaptable filter changing between one of said measurement state and said reference state to the other at least once during each pulse.

11. The method as claimed in claim 9, wherein the adaptable filter comprises a micro-electromechanical system.

12. A gas sensing system including a gas sensor for sensing a gas comprising a light source, a measurement volume and a detector arranged to receive light that has passed through the measurement volume, the system being arranged to:
during a lower energy consumption measurement period, use the detector to make a lower energy consumption measurement of an amount of light received in at least one wavelength band which is absorbed by the gas;
compare said lower energy consumption measurement to a threshold value;
if said threshold value is crossed, during a higher energy consumption measurement period using the detector to make a higher energy consumption measurement of an amount of light received in at least one wavelength band which is absorbed by the gas; and
calculate the concentration of said gas in said measurement volume using the lower energy consumption measurement and/or higher energy consumption measurement;
the gas sensor further comprising a temperature sensor and wherein the gas sensing system is arranged to use a temperature of the gas sensor to configure one or more of a length of the higher energy consumption measurement period, a sampling rate at which the higher energy consumption measurement is carried out or an intensity of the light source during the higher energy consumption measurement period.

13. The gas sensing system as claimed in claim 12, further arranged to carry out said lower energy consumption measurement at a first sampling rate and to carry out said higher energy consumption measurement at a second sampling rate which is higher than the first sampling rate.

14. The gas sensing system as claimed in claim 12, further arranged to carry out said lower energy consumption measurement with the light source at a first intensity and to carry out said higher energy consumption measurement with the light source at a second intensity which is higher than the first intensity.

15. The gas sensing system as claimed in claim 14, wherein said light source has a variable emitting surface area and wherein said second intensity is achieved by increasing the emitting surface area of the light source between said lower energy consumption measurement period and said higher energy consumption measurement period.

16. The gas sensing system as claimed in claim 15, wherein the light source comprises at least two discrete areas able to emit light within the same range of wavelengths, wherein said second intensity is achieved by increasing the number of said discrete areas of the light source which are emitting between said lower energy consumption measurement period and said higher energy consumption measurement period.

17. The gas sensing system as claimed in claim 12, wherein said light source comprises a micro-electro-mechanical system light source.

18. The gas sensing system as claimed in claim 12, further comprising determining one or more of the length of the higher energy consumption measurement period, the sampling rate at which the higher energy consumption measurement is carried out or the intensity of the light source during the higher energy consumption measurement period using the lower energy consumption measurement.

19. The gas sensing system as claimed in claim 12, further arranged to estimate a value of an uncertainty parameter indicative of the level of uncertainty of said lower energy consumption measurement and to determine one or more of the length of the higher energy consumption measurement period, the sampling rate at which the higher energy consumption measurement is carried out or the intensity of the light source during the higher energy consumption measurement period using the value of said uncertainty parameter.

20. The gas sensing system as claimed in claim 12, further arranged to end said higher energy consumption measurement period if the calculated concentration of gas crosses a predetermined threshold.

21. The gas sensing system as claimed in claim 12, further comprising an adaptable filter disposed between the light source and the detector and having a measurement state in which it passes said wavelength band which is absorbed by the gas and a reference state in which said wavelength band is attenuated relative to the measurement state.

22. The gas sensing system as claimed in claim 21, wherein the light source is arranged to emit pulses of light and the adaptable filter is arranged to change between one of said measurement state and said reference state to the other at least once during each pulse.

23. The gas sensing system as claimed in 21, wherein the adaptable filter comprises a micro-electromechanical system.

* * * * *